US00RE48799E

(19) United States
(12) Reissued Patent
Oh

(10) Patent Number: US RE48,799 E
(45) Date of Reissued Patent: Oct. 26, 2021

(54) LASER INTERLOCK SYSTEM FOR MEDICAL AND OTHER APPLICATIONS

(71) Applicant: Samsung Electronics Co., Ltd., Gyeonggi-do (KR)

(72) Inventor: Jung Teak Oh, Seoul (KR)

(73) Assignee: Samsung Electronics Co., Ltd., Suwon-si (KR)

(21) Appl. No.: 15/869,995

(22) Filed: Jan. 12, 2018

Related U.S. Patent Documents

Reissue of:
(64) Patent No.: 9,237,633
Issued: Jan. 12, 2016
Appl. No.: 13/966,834
Filed: Aug. 14, 2013

(30) Foreign Application Priority Data

Aug. 17, 2012 (KR) ..... 10-2012-0090032

(51) Int. Cl.
*G05F 1/00* (2006.01)
*H05B 37/02* (2006.01)
(Continued)

(52) U.S. Cl.
CPC ..... *H05B 47/115* (2020.01); *A61F 9/029* (2013.01); *F16P 3/141* (2013.01); *F16P 3/142* (2013.01); *F16P 3/148* (2013.01); *A61B 5/0095* (2013.01); *A61B 8/429* (2013.01); *F04C 2270/041* (2013.01)

(58) Field of Classification Search
CPC ..... A61B 5/14552; H05B 37/0227
See application file for complete search history.

(56) References Cited

U.S. PATENT DOCUMENTS 4,290,052 A * 9/1981 Eichelberger ..... G06F 3/044 341/33
6,679,838 B2 * 1/2004 Bala ..... A61B 1/042 600/130
(Continued)

FOREIGN PATENT DOCUMENTS

CN 101990417 A 3/2011
CN 103462645 A 12/2013
(Continued)

OTHER PUBLICATIONS

Chinese Search Report dated Apr. 28, 2020.
(Continued)

*Primary Examiner* — Angela M Lie
(74) *Attorney, Agent, or Firm* — Cha & Reiter, LLC

(57) ABSTRACT

A laser interlock system and allows laser radiation to be generated when an inspector and a subject correctly wear safety glasses and during use of a photo-acoustic imaging apparatus, thereby protecting the eyes of the inspector and the subject and preventing unnecessary power consumption. The laser interlock system includes a sensing unit to sense whether or not contact between a user and safety glasses occurs, a light source unit to generate a laser, and a control unit that determines, based on an output value from the sensing unit, whether or not the user is wearing the safety glasses normally, and generates an interlock signal to turn on or off the light source unit for selective laser generation according to the determination.

11 Claims, 20 Drawing Sheets

(51) Int. Cl.

| | |
|---|---|
| ***H05B 39/04*** | (2006.01) |
| ***H05B 41/36*** | (2006.01) |
| ***A61F 9/02*** | (2006.01) |
| ***F16P 3/14*** | (2006.01) |
| ***A61B 8/00*** | (2006.01) |
| ***A61B 5/00*** | (2006.01) |
| ***H05B 47/115*** | (2020.01) |

(56) References Cited

U.S. PATENT DOCUMENTS

| | | | | |
|---|---|---|---|---|
| 8,208,681 | B2 * | 6/2012 | Heller | G06K 9/2054 340/500 |
| 8,564,556 | B2 * | 10/2013 | Lee | G02F 1/13338 178/18.01 |
| 8,977,337 | B2 * | 3/2015 | Oyama | A61B 5/0095 600/407 |
| 9,013,264 | B2 * | 4/2015 | Parshionikar | G08B 21/06 340/3.1 |
| 9,078,617 | B2 * | 7/2015 | Pintel | A61B 8/4438 |
| 2007/0015978 | A1 | 1/2007 | Kanayama et al. | |
| 2007/0258040 | A1 * | 11/2007 | Randall | G02C 11/10 351/158 |
| 2009/0187099 | A1 | 7/2009 | Burcher | |
| 2009/0234228 | A1 | 9/2009 | Pintel et al. | |
| 2012/0116365 | A1 * | 5/2012 | Price | A61B 17/00234 606/1 |
| 2013/0116538 | A1 | 5/2013 | Herzog et al. | |
| 2013/0338478 | A1 * | 12/2013 | Hirota | A61B 8/429 600/407 |
| 2014/0046114 | A1 * | 2/2014 | Nishikawa | A61B 5/06 600/9 |
| 2014/0046166 | A1 * | 2/2014 | Tokita | A61B 5/0095 600/407 |
| 2014/0049190 | A1 * | 2/2014 | Oh | H05B 37/0227 315/307 |
| 2014/0145648 | A1 * | 5/2014 | Tokita | H05B 47/10 315/362 |
| 2014/0204245 | A1 * | 7/2014 | Wexler | H04N 5/23222 348/231.99 |
| 2014/0204331 | A1 * | 7/2014 | Huh | A61F 9/023 351/44 |

FOREIGN PATENT DOCUMENTS

| | | | | |
|---|---|---|---|---|
| CN | 108309248 | A | 7/2018 | |
| CN | 108451546 | A | 8/2018 | |
| JP | 2000-185072 | A | 7/2000 | |
| JP | 2006-525036 | A | 11/2006 | |
| JP | 2008-253377 | A | 10/2008 | |
| KR | 10-2004-0040284 | A | 5/2004 | |
| WO | WO-2011085441 | A1 * | 7/2011 | A61F 9/029 |
| WO | WO-2011162801 | A1 * | 12/2011 | A61B 18/22 |
| WO | 2012/150721 | A1 | 11/2012 | |

OTHER PUBLICATIONS

Chinese Search Report dated Jul. 27, 2020.
Chinese Search Report dated Mar. 10, 2021.
Chinese Search Report dated Apr. 2, 2021.
Chinese Search Report dated Jul. 19, 2021.

* cited by examiner

LASER INTERLOCK SYSTEM FOR MEDICAL AND OTHER APPLICATIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

*This application is a reissue application of U.S. Pat. No. 9,237,633.*

This application claims the benefit of Korean Patent Applications No. 2012-0090032, filed on Aug. 17, 2012 in the Korean Intellectual Property Office, the disclosure of which is incorporated herein by reference.

FIELD OF THE INVENTION

Embodiments of the present invention concern an interlock system to inhibit laser operation laser under particular conditions for use with an ultrasound/photo-acoustic imaging apparatus, for example.

BACKGROUND

A medical imaging system may acquire an image of a subject for diagnosis purposes using transmission, absorption, or reflection of ultrasonic waves, laser light, and X-rays. Such a medical imaging system may comprise an ultrasonic imaging apparatus, a photo-acoustic imaging apparatus, and an X-ray imaging apparatus, for example.

Laser radiation employed by a photo-acoustic imaging system typically has short nanometer-scale wavelengths, and may cause damage to optic nerves of the eyes of any inspector or subject that is directly exposed to the radiation.

Therefore, there is a need for a control system to prevent laser radiation emission except when an inspector or subject is correctly wearing safety glasses or during appropriate use of a photo-acoustic imaging apparatus. A system according to invention principles addresses this need and associated problems.

SUMMARY

A system according to invention principles provides a laser interlock and control system inhibiting laser operation except when an inspector and a subject correctly wear safety glasses or during appropriate use of a photo-acoustic imaging apparatus, thereby protecting the eyes of the inspector and the subject and preventing unnecessary power consumption.

Additional aspects of the invention will be set forth in part in the description which follows and, in part, will be obvious from the description, or may be learned by practice of the invention.

The laser interlock system includes a sensing unit to sense whether or not contact between a user and safety glasses occurs, a light source unit to generate a laser, and a control unit that determines, based on an output value from the sensing unit, whether or not the user normally wears the safety glasses, and generates an interlock signal to turn on or off the light source unit for selective laser generation according to the determined result. The laser interlock system controls a laser generated from an ultrasound/photo-acoustic imaging apparatus, includes an ultrasound data acquisition unit to acquire ultrasound data of a subject, a light source unit to generate the laser, and a control unit to turn on or off the light source unit based on the acquired ultrasound data.

In different embodiments, the sensing unit may be mounted to a nose pad of the safety glasses, may include a capacitive sensor and may include a first substrate, a ground electrode formed on the first substrate, a second substrate bonded onto the ground electrode, and a measurement electrode formed on the second substrate. The sensing unit may also include a left measurement unit and a right measurement unit, and each of the left measurement unit and the right measurement unit may include a first substrate, a ground electrode formed on the first substrate, a second substrate bonded onto the ground electrode, and a measurement electrode formed on the second substrate.

The control unit may include at least one state determiner to determine whether or not a user normally wears safety glasses based on output values of the left measurement unit and the right measurement unit, and an interlock signal generator to generate an interlock release signal for the light source unit if the determined result of the state determiner represents that the user normally wears the safety glasses. The at least one state determiner determines that the user normally wears the safety glasses if each of the output values of the left measurement unit and the right measurement unit exceeds a preset first threshold value. The at least one state determiner determines that the user normally wears the safety glasses if each of the output values of the left measurement unit and the right measurement unit exceeds a preset first threshold value and the output values are maintained for a preset threshold time or more. Further, the at least one state determiner may include a plurality of state determiners, each of which is mounted to the corresponding safety glasses of a plurality of safety glasses, and the interlock signal generator may receive the determined result related to whether or not each user normally wears the corresponding safety glasses from the plurality of state determiners mounted respectively to the plurality of safety glasses. The interlock signal generator generates an interlock release signal for the light source unit if the determined results transmitted from the plurality of state determiners represents that each user normally wears the corresponding safety glasses.

In one embodiment, a laser interlock system controls a laser generated by an ultrasound/photo-acoustic imaging apparatus and includes a sensing unit to sense contact between a subject and a probe, a light source unit to generate the laser, and a control unit to control laser generation by the light source unit based on an output signal from the sensing unit. The sensing unit may include a switch mounted to the probe and the switch may be turned on or off according to whether or not contact between the probe and the subject occurs.

The control unit may turn on the light source unit if the output value of the sensing unit as a determined result represents that contact between the probe and the subject occurs. The control unit also may turn off the light source unit if the output value of the sensing unit as a determined result represents that contact between the probe and the subject does not occur.

The control unit may determine whether or not contact between the probe and the subject occurs based on the output value of the sensing unit, and may control the light source unit based on the determined result. Further, the control unit may be mounted to the probe and may determine that contact between the probe and the subject occurs if the output value of the sensing unit exceeds a preset threshold value. Also, the sensing unit may include a capacitive sensor mounted to a head of the probe and may execute a sensing operation when a pulse signal is not generated from the probe. Further, the sensing unit may include a first substrate, a ground electrode formed on the first substrate, a second substrate bonded onto the ground electrode, and a measurement electrode formed on the second substrate.

The control unit in one embodiment determines whether or not contact between the subject and a probe occurs using the acquired ultrasound data, and may turn on or off the light source unit according to the determined result. The control unit may include an image generator to generate a 2-Dimentional (2D) ultrasound image using the acquired ultrasound data, a profile detector to detect a profile of the subject from the 2D ultrasound image, and a state determiner to compare the detected profile of the subject with profile sample information corresponding to the subject, so as to calculate a profile difference. The state determiner may determine that contact between the subject and the probe occurs if the calculated profile difference is less than a preset threshold value. In accordance with a further aspect of the present invention, a medical appliance includes the laser interlock system according to any one of claims 1 to 28.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
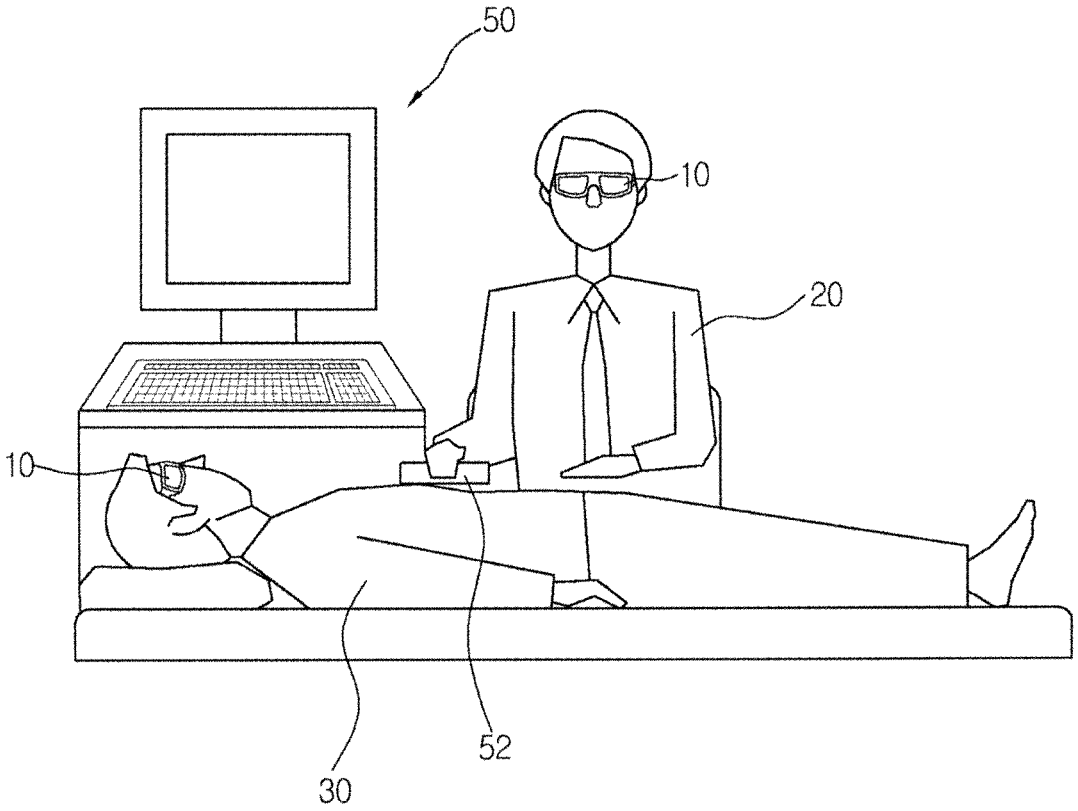
FIG. 1 is a view illustrating diagnosis of a subject using photo-acoustic imaging technology or ultrasound/photo-acoustic imaging technology.

Reference will now be made in detail to the embodiments of the present invention, examples of which are illustrated in the accompanying drawings, wherein like reference numerals refer to like elements throughout.

Ultrasound imaging technology has been widely used as medical imaging technology for diagnosis of a subject. Photo-Acoustic Imaging (PAI) technology combines ultrasonic characteristics and photo-acoustic characteristics of a subject is applied to a variety of diagnostic fields. PAI technology combines high spatial resolution of an ultrasound image with high contrast of an optical image and is suitable for imaging of bodily tissues. As bodily tissues absorb a short electromagnetic pulse of laser radiation having a short nanometer-scale wavelength, momentary generation of ultrasonic waves occurs in the tissues acting as an initial ultrasonic-wave generation source by thermo-elastic expansion. The generated ultrasonic waves reach surfaces of the bodily tissues with various delays, resulting in a photo-acoustic image.

Ultrasound imaging technology is used to diagnose internal diseases of a human body using ultrasonic waves. Ultrasound images may be represented as a B-mode image upon display of an internal cross-sectional image of a subject, an elastic image representing elastic information on a subject, an M-mode image representing vital information on a particular part of a subject and a color-Doppler image visually representing blood flow in real time, for example.

A photo-acoustic image may be used in combination with an ultrasound image. For example, an ultrasound image is acquired by radiating ultrasonic waves to a particular part of a subject, and a photo-acoustic image is acquired by radiating a laser to the same particular part. Through comparison and analysis of the two images, an anatomical configuration and light absorption of the particular part may be concurrently recognized.

In the following description of the embodiments, for description convenience, an apparatus that combines a photo-acoustic imaging apparatus with an ultrasound imaging apparatus is referred to as an ultrasound/photo-acoustic imaging apparatus. A laser interlock system according to an aspect of the present invention may be employed by a single photo-acoustic imaging apparatus and may also be employed by general medical appliances using lasers. Although the laser interlock system may also be employed by an ultrasound/photo-acoustic imaging apparatus that combines a photo-acoustic imaging apparatus with an ultrasound imaging apparatus, in the following embodiments, the laser interlock system is described as being employed by an ultrasound/photo-acoustic imaging apparatus by way of example. The term "normally" as used herein in the wearing of glasses means wearing the glasses in a fashion that protects user eyes from radiation.

FIG. 1 illustrates diagnosing a subject using a photo-acoustic/ultrasound imaging apparatus.

As described above, to acquire a photo-acoustic image, a subject 30 is irradiated with a laser having an extremely short wavelength. However, when the eyes are directly exposed to the laser, this may cause damage to optic nerves.

Accordingly, when diagnosing the subject 30 using an ultrasound/photo-acoustic imaging apparatus 50, as illustrated in FIG. 1, both an inspector 20 and the subject 30 may be required to wear safety glasses 10. The safety glasses 10 serve to protect the eyes from laser radiation from device 52 by blocking the radiated laser to prevent the laser from reaching the eyes. To this end, the safety glasses 10 are configured to absorb light having a particular wavelength band, and wearing safety glasses suitable for the wavelength of radiated laser may be required.

For example, if the laser corresponds to visible light having a shorter wavelength than green, the safety glasses are configured to absorb light having a wavelength of less than 532 nm. If the laser corresponds to red or infrared rays, the safety glasses are configured to absorb light having a wavelength of 600 nm or more.

If laser radiation is emitted in a state in which the inspector 20 or subject 30 do not correctly wear the safety glasses 10, this may cause damage to the eyes of the inspector 20 or subject 30, and radiating a laser while the ultrasound/photo-acoustic imaging apparatus 50 is not in use may cause unnecessary power consumption. Therefore, in the laser interlock system, a light source unit generating a laser is turned on or off in response to the presence/absence of safety glasses or the use/non-use of the ultrasound/photo-acoustic imaging apparatus.

Figure 2:
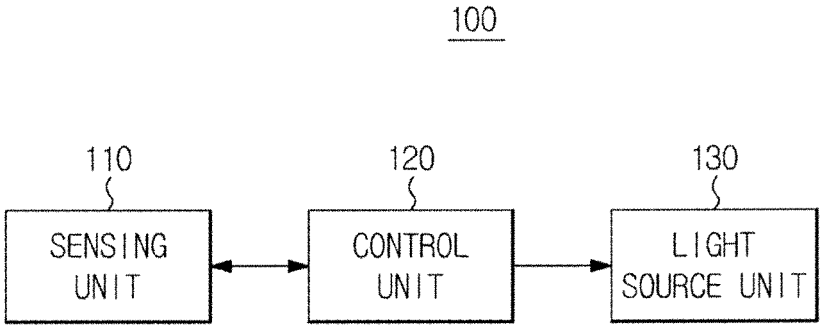
FIG. 2 is a control block diagram of a laser interlock system according to an embodiment of the present invention.

FIG. 2 is a control block diagram of a laser interlock system 100 including a sensing unit 110 to sense contact between safety glasses and an inspector or subject, a control unit 120 to determine whether or not the inspector or subject normally wears the safety glasses based on the sensed result of the sensing unit 110 and to generate radiation using the laser based on the determined result, and a light source unit 130 to be interlocked or released by the control unit 120.

The light source unit 130 may include multiple light sources to generate light of different wavelengths. Each light source is a light emitting device that generates a particular wavelength component or monochromatic light containing the component, such as a semiconductor laser diode (LD), light emitting diode (LED), solid-state laser or gas-laser. In one example, in the case of measuring a density of hemoglobin of a subject, a laser beam having a pulse width of about 10 ns is generated by a Nd-YAG laser (solid-state laser) having a wavelength of about 1000 nm or an He—Ne gas laser having a wavelength of 633 nm. Hemoglobin in a body exhibits different optical absorption properties according to the type thereof, but absorbs light within a range of 600 nm to 1000 nm. A small light emitting device, such as an LD or LED, may be used, which is formed of InGaAlP for a light emission wavelength of about 550~650 nm, formed of GaAlAs for a light emission wavelength of about 650~900 nm, or formed of InGaAs or InGaAsP for a light emission wavelength of about 900~2300 nm. Also, an Optical Parametrical Oscillator (OPO) laser is employed for changing a laser wavelength using nonlinear photonic crystals.

Figure 3:
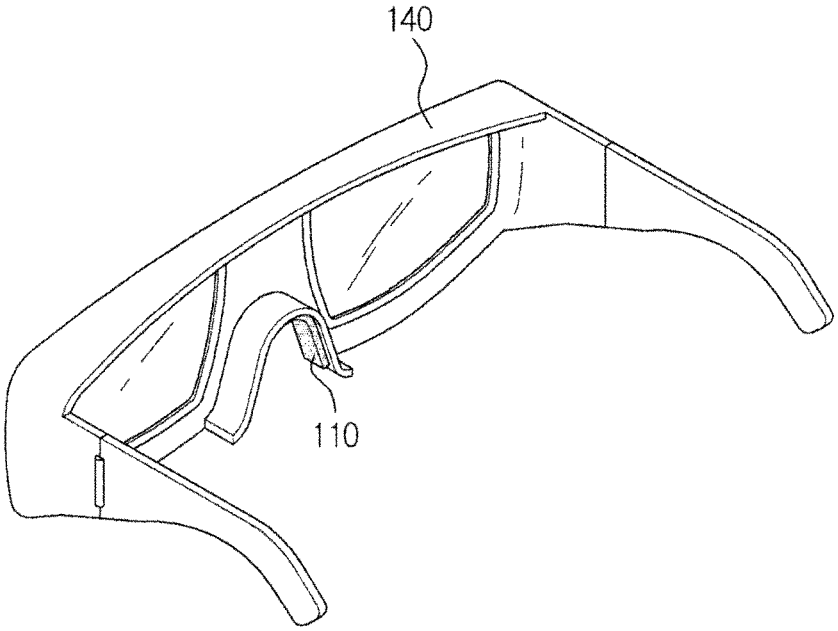
FIG. 3 is a view illustrating an external appearance of safety glasses, to which a sensing unit of a laser interlock system is mounted, according to an embodiment of the present invention.

The sensing unit 110 may be mounted to safety glasses to sense contact between the safety glasses and a human body. Hereinafter, a detailed embodiment of the sensing unit mounted to the safety glasses is described with reference to FIGS. 3 and 4. FIG. 3 illustrates an external appearance of safety glasses, to which a sensing unit of a laser interlock system is mounted. Sensing unit 110 in one embodiment is mounted to a nose pad of safety glasses 140 at a position to come into contact with the nose of a wearer. When an inspector or subject wears the safety glasses 140, the nose of the inspector or subject comes into contact with the sensing unit 110. Thus, an output value of the sensing unit 110 may differ according to whether or not the inspector or subject wears the safety glasses 140. Hereinafter, persons who wear safety glasses during use of the ultrasound/photo-acoustic imaging apparatus, such as the inspector, subject, and the like, are referred to as a user. The sensing unit 110 may be realized by a touch sensor. In an embodiment, a capacitive sensor 110 senses whether or not contact with a human body occurs based on variation of capacitance.

Figure 4A:
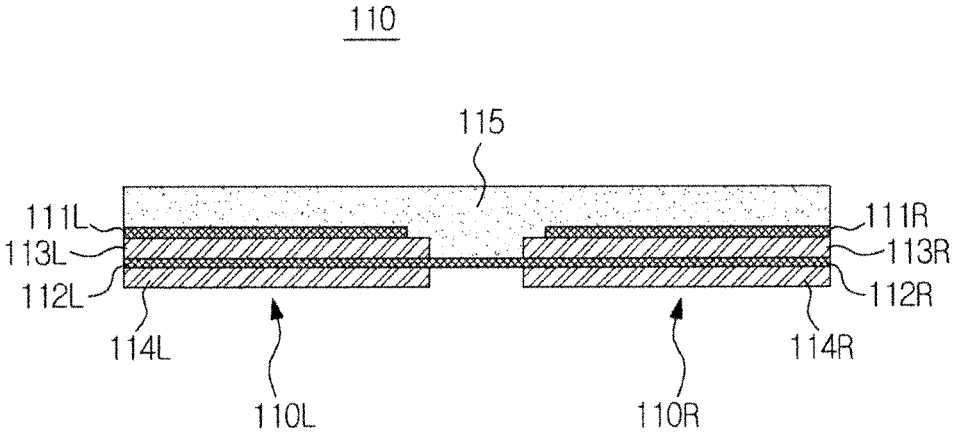
FIGS. 4A and 4B are side views of a sensing unit in the form of a capacitive sensor.
Figure 4B:
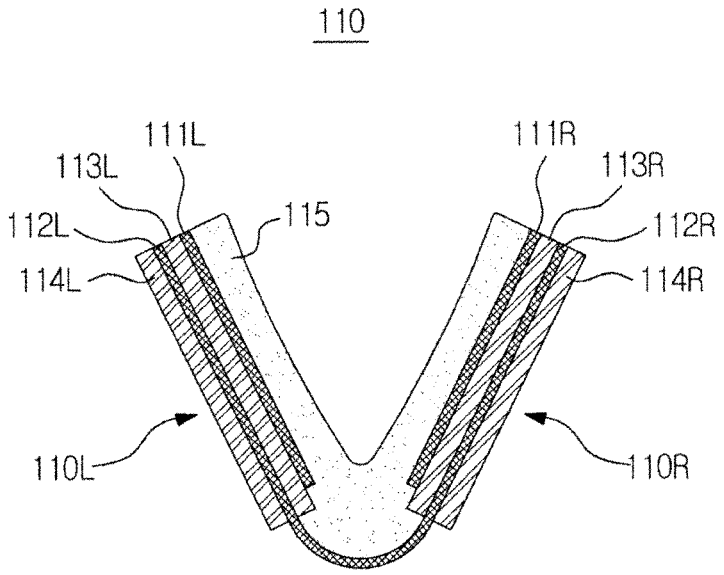

FIGS. 4A and 4B are side views of the sensing unit in the form of a capacitive sensor. In FIG. 4A, the sensing unit 110 includes a left measurement unit 110L and a right measurement unit 110R. The measurement units 110L and 110R respectively include measurement electrodes 111L and 111R and ground electrodes 112L and 112R. The measurement electrodes 111L and 111R and ground electrodes 112L and 112R are respectively installed or formed on first substrates 113L and 113R and second substrates 114L and 114R. A soft polymer 115 is bonded to the measurement electrodes 111L and 111R, which may eliminate discomfort due to direct contact with the measurement electrodes 111L and 111R when the user wears safety glasses. Bonding of the polymer may be achieved via injection molding, and various other known methods.

The ground electrode 112L included in the left measurement unit 110L and the ground electrode 112R included in the right measurement unit 110R may be integrated. When the sensing unit 110 is attached to the safety glasses 140, as illustrated in FIG. 4B, the sensing unit 110 may be attached in a bent state to correspond to the shape of the nose pad of the safety glasses 140.

The measurement electrodes 111L and 111R may be formed of a copper plate, and the polymer 115 may be polyurethane. To optimize contact sensitivity, an area of the measurement electrodes 111L and 111R may be 6 mm×15 mm, and a distance between the two measurement electrodes 111L and 111R may be 0.5 mm, and a thickness of the polymer 115 may be 1.5 mm. These dimensions and materials are given by way of example to realize the sensing unit 110 according to one embodiment of the invention, and the embodiment is not limited thereto.

Figure 5A:
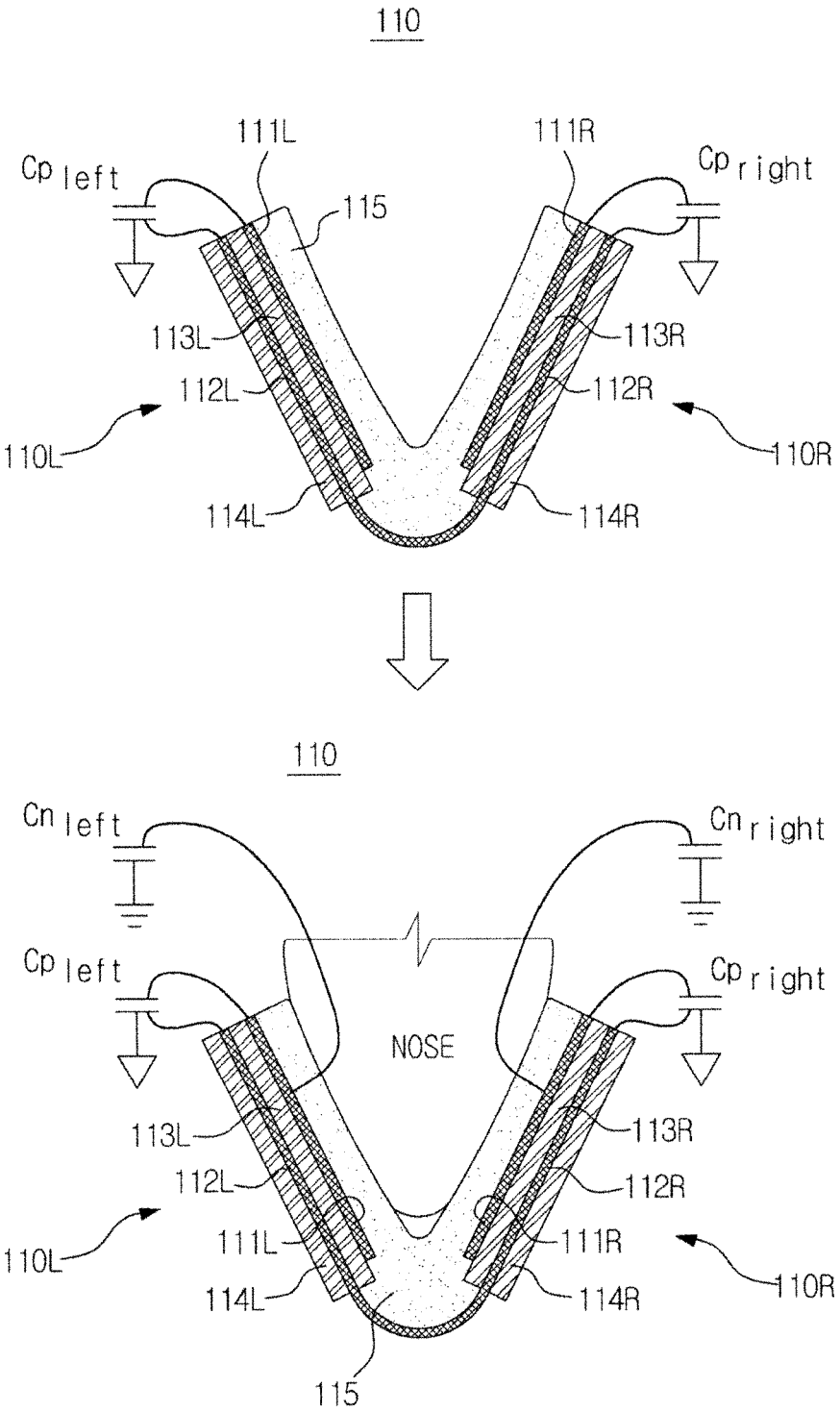
FIG. 5A is a side view of a sensing unit to output capacitance.
Figure 5B:
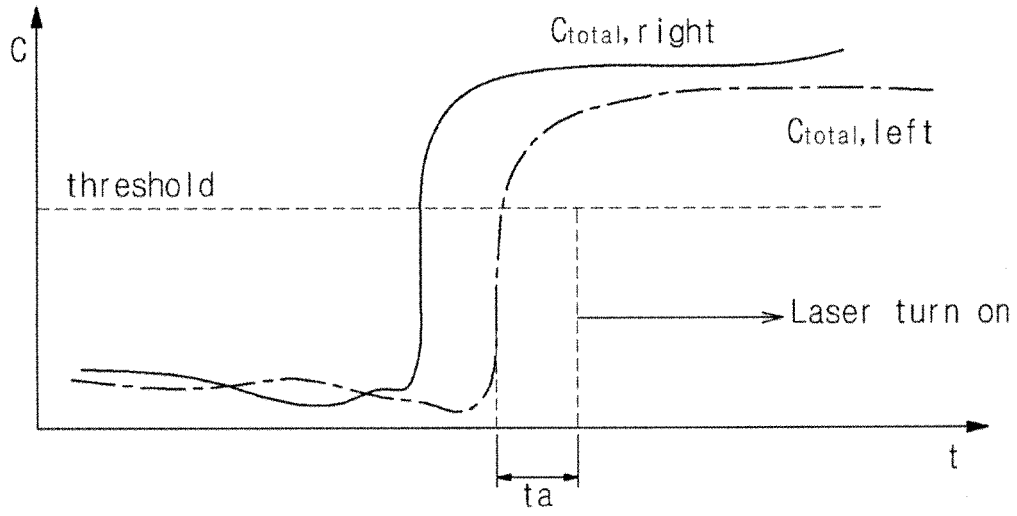
FIG. 5B is a graph illustrating variation of capacitance output by a sensing unit.

FIG. 5A shows side views of the capacitive sensing unit, and FIG. 5B is a graph illustrating variation of capacitance output by the sensing unit. Referring to FIG. 5A, in a state in which the user does not wear the safety glasses 140, capacitance values $Cp_{left}$ and $Cp_{right}$ between the ground electrodes 112L and 112R and the measurement electrodes 111L and 111R of the left measurement unit 110L and the right measurement unit 110R, respectively, are measured. If the user wears the safety glasses 140 and the nose of the user touches the polymer 115, the nose of the user acts as a ground electrode through the body of the user. Thus, capacitance values $Cn_{left}$ and $Cn_{right}$ are measured between the nose of the user and the measurement electrodes 111L and 111R, and consequently the measured capacitance values are increased. Output values $Ctotal_{left}$ and $Ctotal_{right}$ of the left measurement unit 110L and the right measurement unit 110R are represented by the following Equation 1.

Equation 1

$$C_{total,\ left}=C_{p,\ left}+C_{n,\ left}$$

$$C_{total,\ right}=C_{p,\ right}+C_{n,\ right}$$

As illustrated in FIG. 5B, if an output value of the left measurement unit 110L and an output value of the right measurement unit 110R exceed a predetermined threshold value and this state is continued for a predetermined threshold time $t_a$, it is determined that the user is wearing the safety glasses 140 normally.

Figure 6:
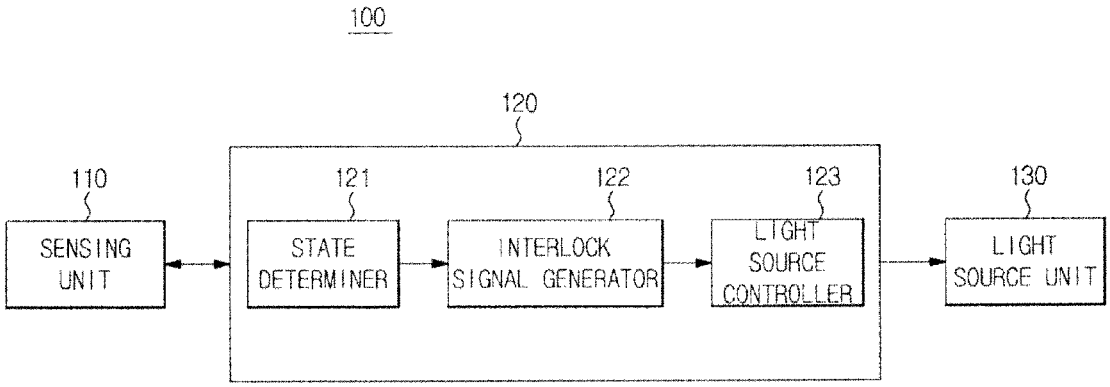
FIG. 6 is a control block diagram illustrating a configuration of a control unit in a laser interlock system according to an embodiment of the present invention.

FIG. 6 shows a control block diagram illustrating a configuration of a control unit in a laser interlock system. Control unit 120 includes a state determiner 121 that acquires a capacitive signal from the sensing unit 110 and determines whether or not the user wears the safety glasses 140, i.e. the state of the safety glasses 140 based on the acquired capacitive signal. Unit 120 also includes an interlock signal generator 122 that generates an interlock signal based on the state of the safety glasses 140, and a light source controller 123 that controls the light source unit 130 in response to the interlock signal.

The state determiner 121, acquires an output value of the left measurement unit 110L and an output value of the right measurement unit 110R from the sensing unit 110. If there is a single capacitance measurement channel, the output value of the left measurement unit 110L and the output value of the right measurement unit 110R may be acquired sequentially respectively using a multiplexer. The state determiner 121 determines the state of the safety glasses 140 based on the output values acquired from the sensing unit 110. In an embodiment, a minimum value that may be acquired from the sensing unit 110 when a human body comes into contact with the polymer 115 is set to a threshold value. When the output values acquired from both the measurement units 110L and 110R exceed the threshold value, it is determined that the user wears the safety glasses 140. Also, to detect the case in which the user does not normally wear the safety glasses 140, it is determined that the user wears the safety glasses 140 if the output values of both the measurement units 110L and 110R are maintained for a predefined threshold time or more. The results are transmitted to the interlock signal generator 122.

The state determiner 121 also controls acquisition of capacitance. Specifically, if it is determined that the user normally wears the safety glasses, the state determiner 121 stop acquisitions of the capacitive signal, acquires the capacitive signal for a predetermined period, or alternatively acquire the output value of the left measurement unit 110L and the output value of the right measurement unit 110R at a constant time interval.

The interlock signal generator 122 generates an interlock signal based on the state of the safety glasses 140 determined by the state determiner 121. The interlock signal refers to an interlock setting signal or an interlock release signal. A signal to release the light source unit 130 from an interlocked state thereof is an interlock release signal, and a signal to interlock the released light source unit 130 and inhibit radiation emission is an interlock setting signal. In an embodiment, if the state determiner 121 determines that the user wears the safety glasses 140 in an interlocked state of the light source unit 130, the interlock signal generator 122 generates an interlock release signal and transmits the signal to the light source controller 123. In this case, the generated interlock signal may be a Transistor to Transistor Logic (TTL) signal.

The light source controller 123 turns on the light source unit 130 if an interlock release signal is input in an interlocked state of the light source unit 130, and turns off the light source unit 130 if an interlock setting signal is input in an interlock-released state of the light source unit 130.

Figure 7:
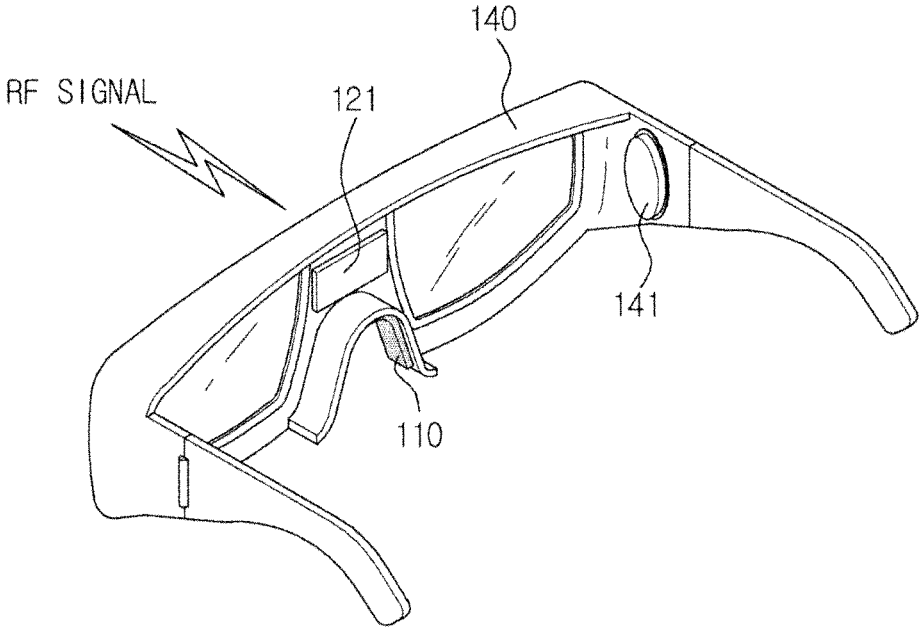
FIG. 7 is a view illustrating an external appearance of safety glasses, to which some parts of a control unit are mounted, in a laser interlock system according to an embodiment of the present invention.

FIG. 7 is a view illustrating an external appearance of safety glasses, to which some parts of the control unit are mounted. Elements of the control unit 120 state determiner 121 comprising a microcontroller (MCU) mounted to the safety glasses 140. Thus, the state determiner 121 acquires a capacitive signal measured by the sensing unit 110 and directly uses the capacitive signal without additional signal processing or conversion.

The state of the safety glasses 140 determined by the state determiner 121 is transmitted to the interlock signal generator 122 in a wired or wireless manner. In the case of wireless transmission, the state of the safety glasses 140 may be converted into an RF signal to be transmitted. Of course, the signal transmission of the present embodiment is not limited to RF signal transmission, and various other wireless communication methods may be alternatively be employed.

A battery 141 supply power of the sensing unit 110 and the MCU of the safety glasses 140 is mounted to the safety glasses 140. This may advantageously eliminate connection of a separate power cable to the safety glasses 140.

The other elements of the control unit 120 may be installed at a workstation or console to control operations of the ultrasound/photo-acoustic imaging apparatus. Of course, the embodiment of the present invention is not limited to the mounting or installation positions of the respective elements of the control unit 120, which may be mounted at location of any of the system elements so long as functions thereof can be executed.

Figure 8:
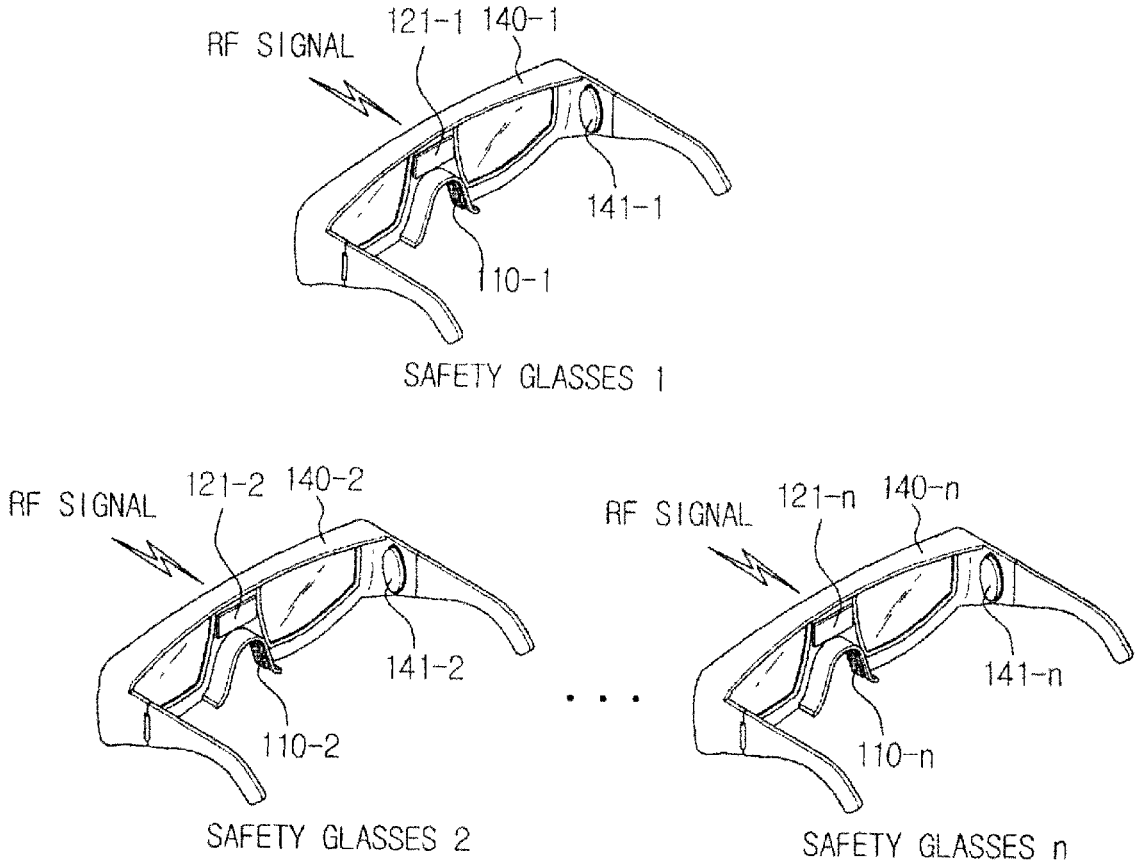
FIG. 8 is a view illustrating an overall configuration of a laser interlock system to control interlock of lasers according to the state of a plurality of safety glasses.

FIG. 8 shows an overall configuration of a laser interlock system to control interlock of a laser according to the state of a plurality of safety glasses. Plurality of safety glasses 140 are registered on a single layer interlock system 100. Specifically, when using a single ultrasound/photo-acoustic imaging apparatus, multiple users may be involved comprising a person affected by a laser radiated from the corresponding apparatus including an inspector, subject, assistant, and the like.

If the number of users is three or more ($n \geq 3$), for example, a plurality of safety glasses 140-1, 140-2, . . . , 140-n may be provided respectively with sensing units 110-1, 110-2, . . . , 110-n and state determiners 121-1, 121-2, . . . , 121-n. The state determiners 121-1, 121-2, . . . , 121-n of the respective safety glasses 140 transmit wireless signals representing the state of the respective safety glasses 140, i.e., the determined results with respect to whether or not the users normally wear the respective safety glasses 140-1, 140-2, . . . , 140-n, such as RF signals, for example, to the interlock signal generator 122. The interlock signal generator 122 transmits an interlock release signal to the light source controller 123 when the users normally wear the plurality of safety glasses 140-1, 140-2, . . . , 140-n. Unit 122 transmits an interlock setting signal if at least one of the users does not normally wear the safety glasses 140-1, 140-2, . . . , 140-n.

Alternatively, if a single pair of safety glasses are registered on the ultrasound/photo-acoustic imaging apparatus, a signal based on the determined result of whether or not contact occurs, output from the state determiner 121, may be an interlock signal. Therefore, in an embodiment omission of the interlock signal generator 122 may be possible. If the number of registered safety glasses is constant, the number of users may differ whenever the ultrasound/photo-acoustic imaging apparatus is used. Thus, to prevent a laser from being unnecessarily interlocked by a capacitive signal output from safety glasses that are not actually used, a user selects safety glasses that the user actually wears during use of the ultrasound/photo-acoustic imaging apparatus using an input unit provided at the apparatus. Here, the input unit may be provided at a workstation or console of the ultrasound/photo-acoustic imaging apparatus. Each pair of safety glasses may be provided with an identifier. Once safety glasses have been selected, the sensing unit mounted to the selected safety glasses acquires a capacitive signal, and transmits a signal representing the state of the safety glasses to the interlock signal generator. Alternatively, safety glasses may be provided with an ON/OFF button such that the state determiner is operated when a user pushes the button.

Although the above-described embodiment describes the state determiner 121 of the control unit 120 as being mounted to the safety glasses 140, the embodiment is given by way of example, and the embodiments of the present invention are not limited in terms of installation positions of the respective constituent elements of the control unit 120.

In the description related to FIGS. 2 to 8, embodiments are described where it is determined a user wears safety glasses in response to contact between the user and the safety glasses and in response a laser is interlocked when a user does not wear the safety glasses. Hereinafter, an embodiment of the laser interlock system is described where interlock of a laser occurs in response to use of ultrasound/photo-acoustic imaging apparatus.

Figure 9:
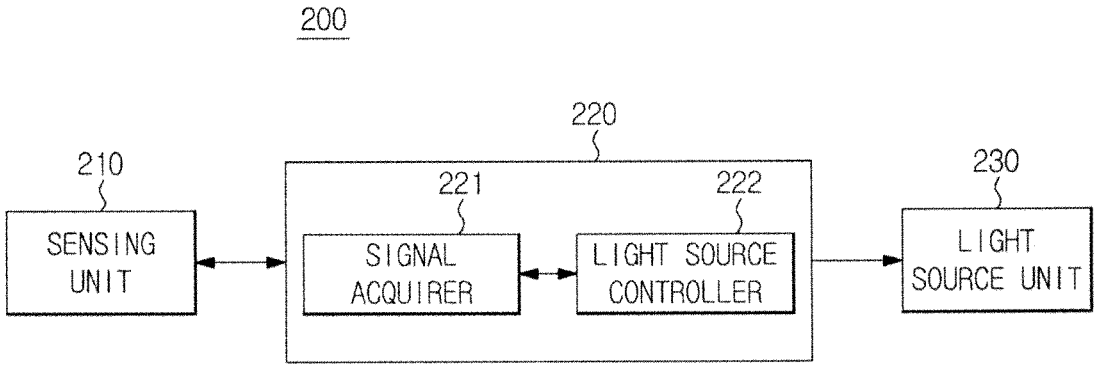
FIG. 9 is a control block diagram of a laser interlock system according to another embodiment of the present invention.

FIG. 9 is a control block diagram of laser interlock system 200 including a sensing unit 210 to sense contact between a probe and a human body, a control unit 220 to control a light source unit 230 according to the sensed result of the sensing unit 210, and light source unit 230 generates a laser under control of the control unit 220. The laser interlock system 200 determines whether or not the ultrasound/photo-acoustic imaging apparatus is used based on whether or not contact between a probe and a subject occurs. That is, if contact between the probe and the subject occurs, it is determined that the ultrasound/photo-acoustic imaging apparatus is used. Here, the probe may consist of a general ultrasound probe to transmit and receive ultrasonic waves and a bundle of optical fibers mounted to the ultrasound probe to radiate laser beams.

The sensing unit 210 is mounted to the probe and senses contact between the probe and the subject. Contact sensing methods include a mechanical method and an electric method. The laser interlock system 200 employs a mechanical method to sense contact between the probe and the subject. Hereinafter, a detailed embodiment thereof is given with reference to the drawings.

Figure 10A:
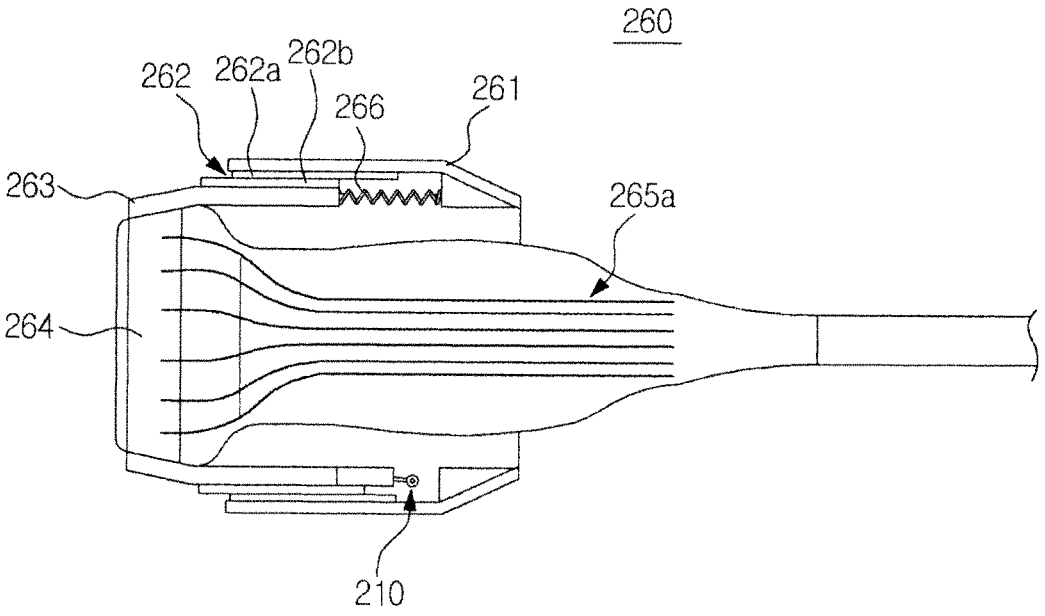
FIGS. 10A, 10B and 10C are sectional views illustrating a probe used in a laser interlock system and a sensing unit mounted to the probe to mechanically sense contact according to another embodiment of the present invention.
Figure 10B:
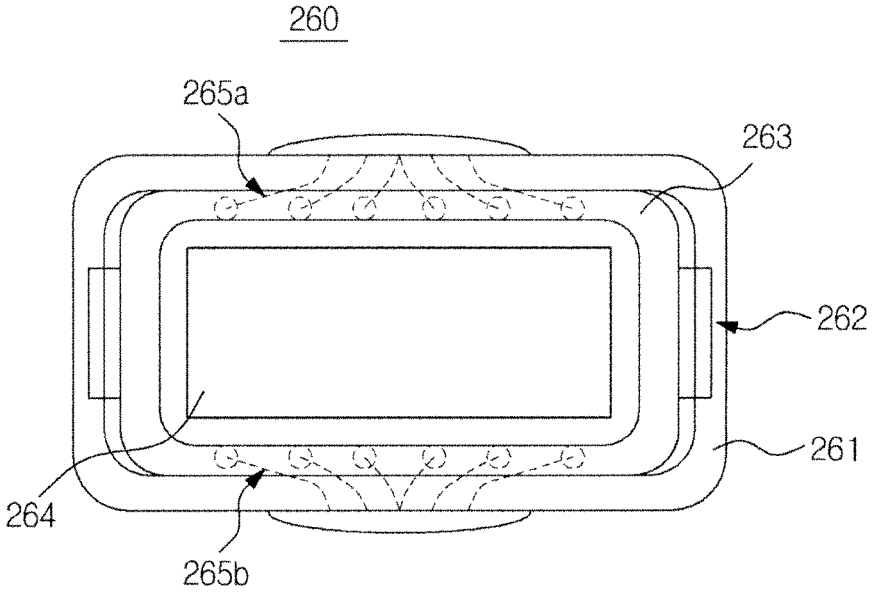
Figure 10C:
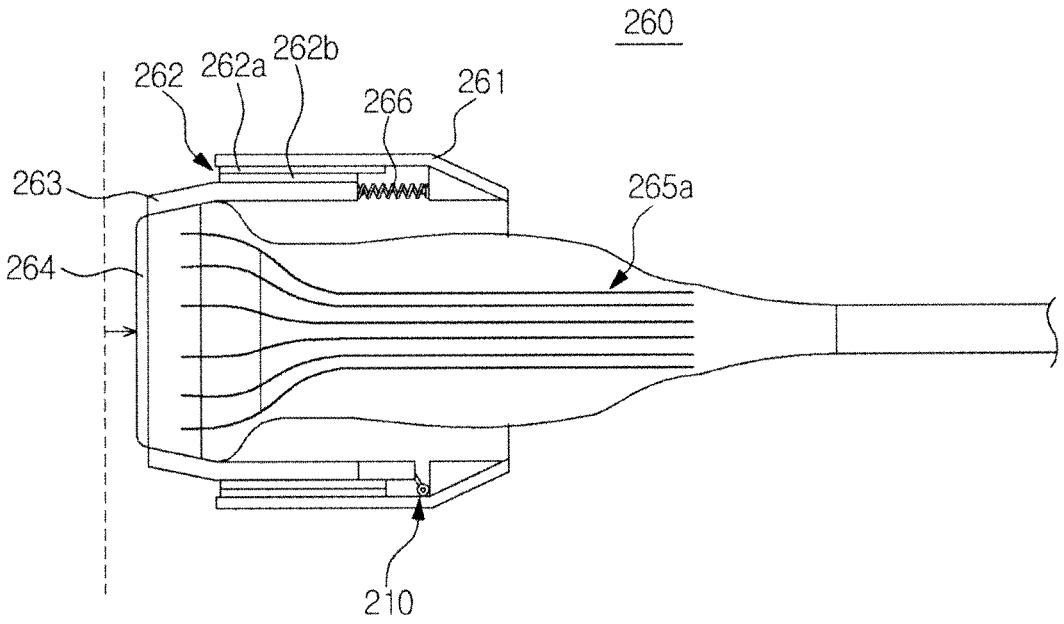

FIGS. 10A, 10B and 10C are sectional views illustrating a probe used in a laser interlock system and a sensing unit mounted to the probe to mechanically sense contact. Assuming that a plane to which ultrasonic waves and a laser are radiated is referred to as a front plane, FIG. 10A and 10C are sectional plan views of the probe and FIG. 10B is a front view of the probe.

Referring to FIG. 10A, a probe 260 includes an ultrasound probe 264 to transmit and receive an ultrasonic signal, and a bundle of optical fibers 265 to radiate a laser. The ultrasound probe 264 accommodates a plurality of converters (not shown) to change an ultrasonic signal into an electric signal or to change an electric signal into an ultrasonic signal. Bundles of optical fibers 265a and 265b may respectively provided above and below the converters to transmit a laser generated from the light source unit 230 to a subject.

The ultrasound/photo-acoustic imaging apparatus may apply a [pulsar] *pulse* signal corresponding to a momentary high-pressure signal to the inner elements of the probe 260, and the inner elements of the probe 260 may be shielded from the outside for safety. In the case of optical fibers transmitting a high-energy laser, a hot spot occurs, which may cause damage or need for replacement. Thus, the probe 260 according to the present embodiment is described as the ultrasound probe 264, i.e. a region in which the converters are located being separated from a laser transmission region (the bundles of optical fibers 265a and 265b).

Referring to FIGS. 10A and 10B together, a moving piece 263 is configured to surround the ultrasound probe 264 containing the plurality of converters therein, and is fixed to the ultrasound probe 264. One end of each of the bundles of optical fibers 265a and 265b is fixed to the moving piece 263 to maintain a constant distance between the ultrasound probe 264 and the end of each of the bundles of optical fibers 265a and 265b. A probe handle 261 is formed around the moving piece 263 to surround the moving piece 263. A guide unit 262 is interposed between the moving piece 263 and the probe handle 261 to guide linear movement of the moving piece 263. The guide unit 262 consists of a first guide 262a installed to the probe handle 261 and a second guide 262b installed to the moving piece 263.

If an inspector pushes an ultrasonic signal transmission/reception surface of the probe 260 onto a diagnosis region of a subject while gripping the probe handle 261, the ultrasound probe 264 and the moving piece 263 fixed thereto are retracted along the guide unit 262 in a direction opposite to the subject as illustrated in FIG. 10C. In this case, an end of the probe handle 261 may be bent toward the ultrasound probe 264, and an elastic piece 266, such as a spring, may be mounted between the end of the probe handle 261 and an end of the moving piece 263, which allows the moving piece 263 to be returned to an original position thereof when pressure is no longer applied to the ultrasonic signal transmission/reception surface.

The sensing unit 210 may be mounted to the other end of the moving piece 263 to which the elastic piece 266 is not mounted. The sensing unit 210 may take the form of a switch, such as a micro-switch. If the moving piece 263 is retracted as pressure is applied to the ultrasonic signal transmission/reception surface, the switch 210 mounted to the end of the moving piece 263 is pushed by the end of the probe handle 261 or a structure formed at the end as illustrated in FIG. 10C. Since the switch 210 is pushed when the subject comes into contact with the probe 260 and is not pushed while the subject does not come into contact with the probe 260, an output value of the sensing unit 210 differs according to whether or not the subject comes into contact with the probe 260. Of course, the configuration of the sensing unit 210 as described above with reference to FIGS. 10A, 10B and 10C are given by way of example, and the kind and installation position of the sensing unit are not limited to the above-described embodiment.

Referring again to FIG. 9, the control unit 220 includes a signal acquirer 221 to acquire an output signal from the sensing unit 210, and a light source controller 222 to turn on or off the light source unit 230 according to the output signal of the sensing unit 210. The signal acquirer 221 may acquire the output signal of the sensing unit 210 in real time or for a predetermined period.

Assuming that the sensing unit 210 takes the form of a switch, an output signal of the sensing unit 210 is transmitted to the signal acquirer 221 if the switch is pushed. The light source controller 222 turns on the light source unit 230 if the signal acquirer 221 acquires a switch-on signal in an interlocked state of the light source unit 230, and turns off the light source unit 230 if the signal acquirer 221 acquires a switch-off signal in an interlock-released state. The output signal of the switch is an ON/OFF signal, and thus may serve as an interlock signal.

Figure 11:
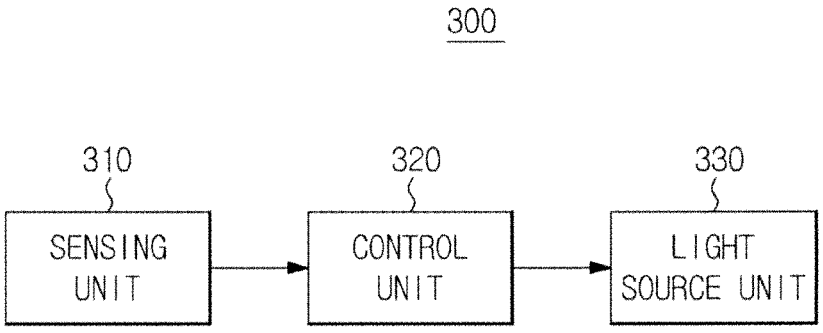
FIG. 11 is a control block diagram of a laser interlock system according to another embodiment of the present invention.

FIG. 11 is a control block diagram of a laser interlock system. Although the laser interlock system according to the present embodiment is similar to the previously described embodiment in terms of generating a laser based on the determined result of whether or not contact between a subject and a probe occurs, whether or not contact between the subject and the probe may be electrically sensed differently from previously described embodiment.

Referring to FIG. 11, a laser interlock system 300 includes a sensing unit 310 to electrically sense contact between a probe and a subject, a light source unit 330 to generate a laser, and a light source control unit 320 that determines whether or not contact between the subject and the probe occurs according to the sensed result of the sensing unit 310 and controls the light source unit 330 according to the determined result.

Figure 12A:
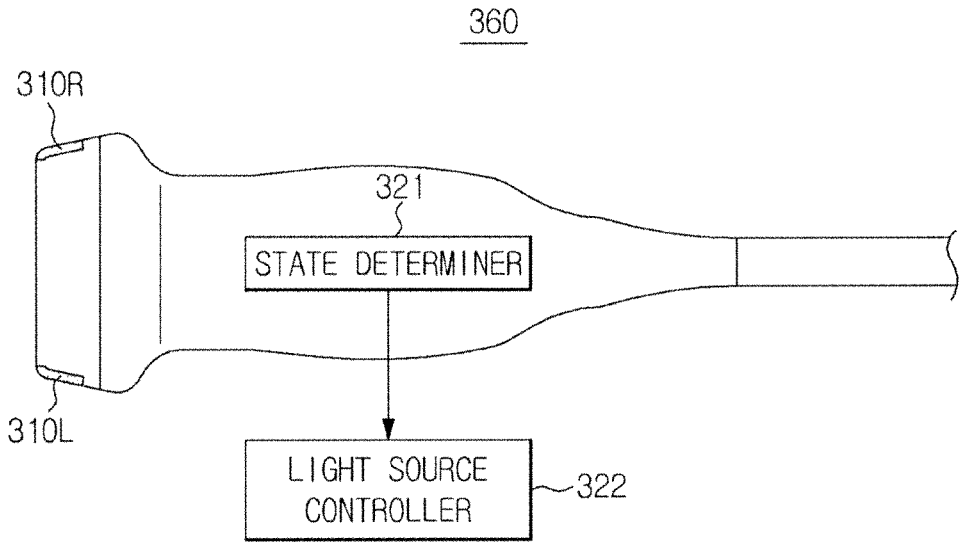
FIGS. 12A and 12B are sectional views illustrating a probe used in a laser interlock system and a sensing unit mounted to the probe to electrically sense contact according to another embodiment of the present invention.
Figure 12B:
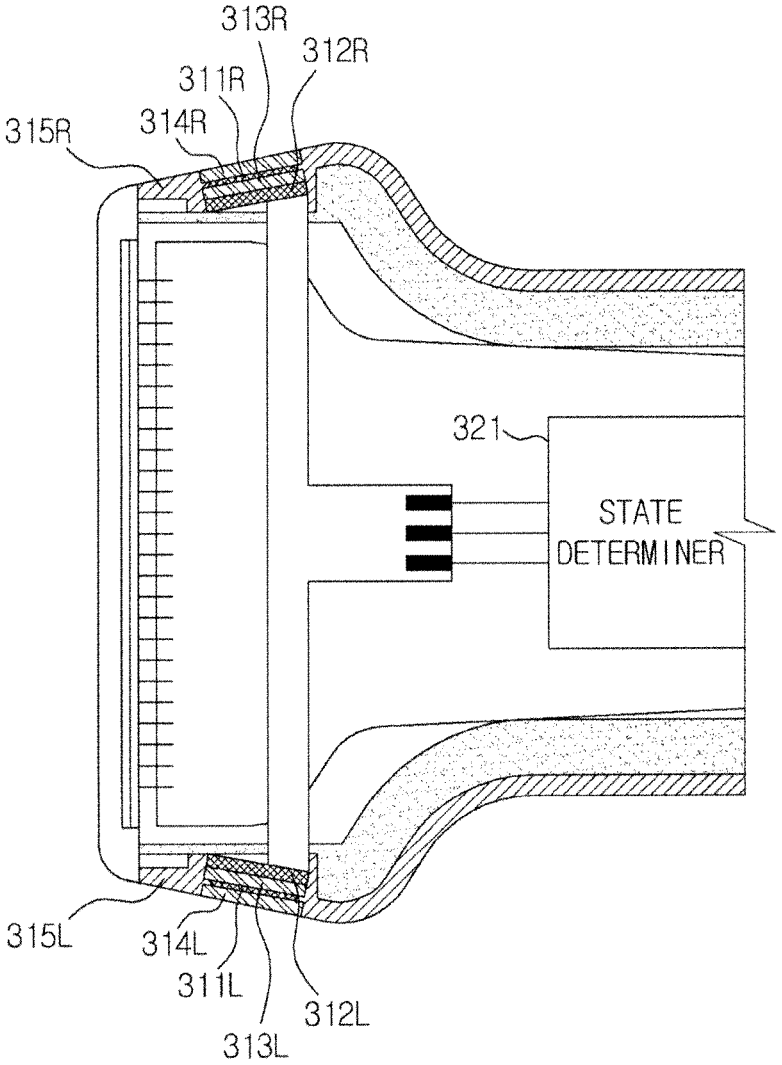

FIGS. 12A and 12B show sectional views illustrating a probe 360 used in the laser interlock system 300 and the sensing unit 310 mounted to the probe 360 to electrically sense contact between the probe 360 and the subject according to another embodiment of the present invention. Although the probe 360 illustrated in FIGS. 12A and 12B includes a bundle of optical fibers to radiate a laser, illustration thereof is omitted for convenience of description.

As described above in relation to the embodiment of FIG. 4, contact between a sensor and a subject may be electrically sensed using the sensing unit 310 as a capacitive sensor. Thus, in the present embodiment, the capacitive sensor is mounted to the probe 360, and the control unit 320 determines whether or not the subject comes into contact with the probe 360 by analyzing an output value of the capacitive sensor.

Referring to FIG. 12A, the sensing unit 310 in the form of a capacitive sensor may be mounted to a head of the probe 360. To achieve reliable sensing, sensing units 310L and 310R may be mounted respectively to a left end and a right end of the head of the probe 360. Thus, the sensing unit 310 includes a right measurement unit 310R and a left measurement unit 310L.

Referring to FIG. 12B, the right measurement unit 310R and the left measurement unit 310L respectively include first substrates 312R and 312L, ground electrodes 313R and 313L formed on the first substrates 312R and 312L, second substrates 311R and 311L, and measurement electrodes 314R and 314L formed on the second substrates 311R and 311L. Polymer housings 315R and 315L, for example, urethane housings may surround the probe 360, and the right measurement unit 310R and the left measurement unit 310L may be fixed to the urethane housings. Here, the second substrates 311R and 311L formed between the ground electrodes 313R and 313L and the measurement electrodes 314R and 314L may serve as dielectrics storing electric charge, and the ground electrode 313R of the right measurement unit and the ground electrode 313L of the left measurement unit may be connected to each other. As illustrated in FIGS. 12A and 12B, inserting the ground electrodes 313R and 313L into the probe 360 may minimize a negative effect due to pulse generation.

Capacitance is created between the ground electrodes 313R and 313L and the measurement electrodes 314R and 314L of the respective measurement units, and is also created between the subject and the measurement electrodes 314R and 314L when the subject comes into contact with the probe 360. Thus, an output value of the sensing unit 310 differs according to whether or not the subject comes into contact with the probe 360.

The control unit 320 includes a state determiner 321 to determine whether or not the subject comes into contact with the probe 360 using the output value of the sensing unit 310, and a light source controller 322 to turn on or off the light source unit 330 according to the determined result of the state determiner 321.

The output value of the sensing unit 310 is input to the state determiner 321. Referring again to FIG. 12A, the state determiner 321 may be a microcontroller (MCU) mounted within the probe 360. The embodiment of the present invention is not limited with regard to the mounting or installation positions of the respective elements of the control unit 320, which may be mounted on different units of the system so long as functions thereof can be executed.

The state determiner 321 determines whether or not the subject comes into contact with the probe 360 based on the output value of the sensing unit 310. In an embodiment, it may be determined that the subject comes into contact with the probe 360 if the output value of the sensing unit 310 exceeds a preset threshold value. Here, the preset threshold value may be a minimum value that may be output when a human body comes into contact with the sensing unit 310.

A signal related to the determined result of the state determiner 321 may be an interlock signal. A signal representing that the probe 360 comes into contact with the subject is an interlock release signal, and a signal representing that the probe 360 does not come into contact with the subject is an interlock setting signal. Thus, based on the determined result from the state determiner 321, the light source controller 322 turns on the light source unit 330 if the subject comes into contact with the probe 360, and turns off the light source unit 330 if the subject does not come into contact with the probe 360.

The sensing operation of the sensing unit 310 is performed when no pulse is generated within the probe 360. Thus, an output value from the sensing unit 310 is acquired when no pulse is generated within the probe 360. For example, when acquiring an ultrasound image having a depth of 5 cm, it may be necessary to acquire an output value from the sensing unit 310 within a very short time because the pulse duration is less than 3.3 μsec.

To this end, in an embodiment, constant current is supplied to the sensing unit 310 for a predetermined time to directly measure a voltage of each measurement unit, and the measured voltage is input to a comparator provided in the state determiner 321. Based on the result from the state determiner 321, whether or not contact between the probe 360 and the subject occurs may be determined. Specifically, assuming that a threshold voltage input to the comparator is a minimum voltage indicating contact between the sensing unit 310 and the subject, a signal value of '0' or '1' is output according to whether or not contact between the sensing unit 310 and the subject occurs. The signal output from the comparator may be an interlock signal. The interlock signal is transmitted to the light source controller 322 to release the light source unit 330 from an interlocked state thereof or to keep the light source unit 330 interlocked.

In the embodiment described in FIGS. 9 to 12, whether or not contact between the probe and the subject occurs is determined using the sensor mounted to the probe. In the following embodiment, whether or not contact between the probe and the subject occurs is determined using ultrasound data on the subject.

Figure 13:
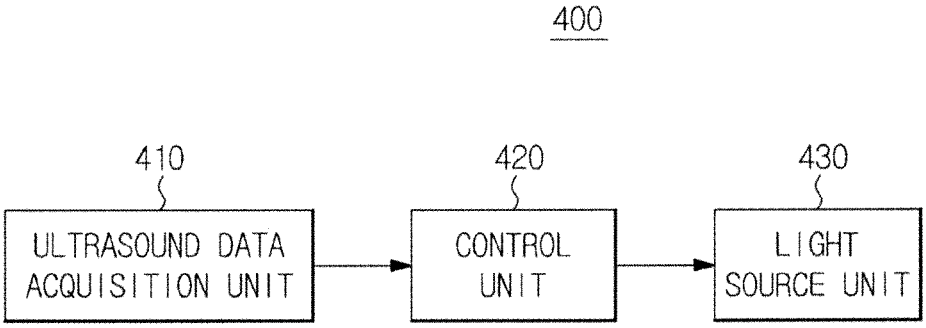
FIG. 13 is a control block diagram of a laser interlock system to determine whether or not a probe comes into contact with a subject using ultrasound data on the subject.
Figure 14:
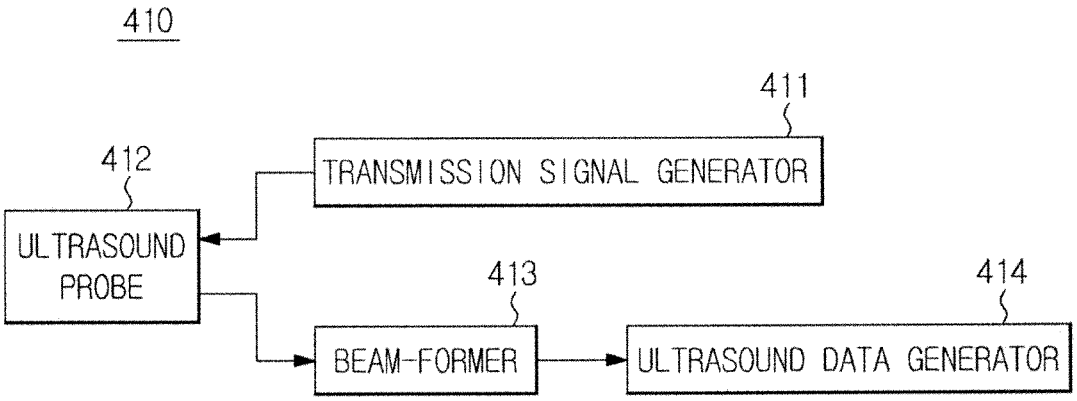
FIG. 14 is a control block diagram illustrating a configuration of an ultrasound data acquisition unit.
Figure 15:
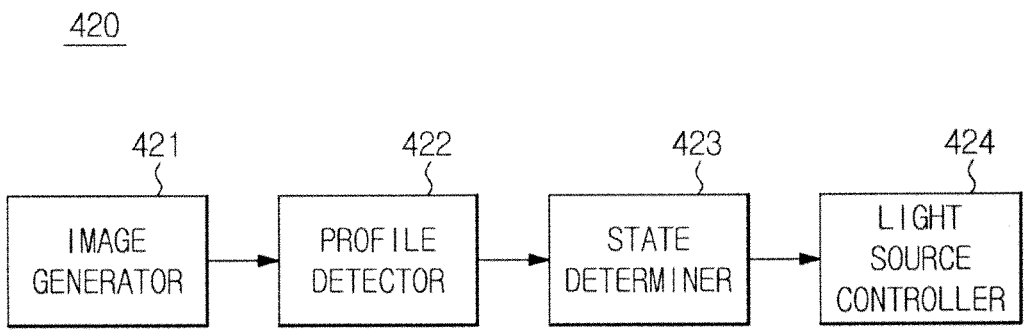
FIG. 15 is a control block diagram illustrating a configuration of a control unit.

FIG. 13 shows a control block diagram of a laser interlock system to determine whether or not a probe comes into contact with a subject using ultrasound data on the subject, FIG. 14 shows a control block diagram illustrating a configuration of an ultrasound data acquisition unit, and FIG. 15 shows a control block diagram illustrating a configuration of a control unit.

Referring to FIG. 13, the laser interlock system 400 includes an ultrasound data acquisition unit 410 that acquires ultrasound data on a subject, a control unit 420 that determines whether or not contact between a probe and the subject occurs based on the acquired ultrasound data and generates a laser interlock signal based on the determined result, and a light source unit 430 that generates a laser in response to the interlock signal.

The ultrasound data acquisition unit 410 transmits an ultrasonic signal to the subject, and acquires ultrasound data upon receiving the ultrasonic signal reflected from the subject. Referring to FIG. 14, the ultrasound data acquisition unit 410 includes a transmission signal generator 411, an ultrasound probe 412 containing a plurality of converters therein, a beam-former 413, and an ultrasound data generator 414.

The transmission signal generator 411 generates a transmission signal required to obtain a plurality of image frames in consideration of positions and focal points of converters. The transmission signal generator 411 repeatedly performs generation of a transmission signal for the individual image frames.

Upon receiving the transmission signal from the transmission signal generator 411, the ultrasound probe 412 changes the transmission signal into an ultrasonic signal to transmit the ultrasonic signal to the subject, and generates a reception signal upon receiving an ultrasonic echo signal reflected from the subject. The reception signal may be an analog signal, and the ultrasound probe 412 may be a 3D probe or 2D array probe, although there is no limit as to the kind of the ultrasound probe. The ultrasound probe 412 may be within the probe as described above in FIGS. 10 to 12.

The beam-former 413 changes the received signal from the ultrasound probe 412 into a digital signal via analog to digital conversion. Additionally, the beam-former 413 applies a time delay to the digital signal in response to delay associated with position of the converters and focal points of signals being processed by the converters, thereby generating a delay compensated digital focused reception signal.

The ultrasound data generator 414 generates ultrasound data using the focused reception signal from the beam-former 413. The ultrasound data may be RF or In-phase/Quadrature (IQ) data. The ultrasound data generator 414 may perform various forms of signal processing required to generate ultrasound data (for example, gain adjustment and filtering).

Referring to FIG. 15, the control unit 420 includes an image generator 421, a profile detector 422, a state determiner 423, and a light source controller 424. The image generator 421 generates a 2D ultrasound image using the ultrasound data that is successively transmitted from the ultrasound data acquisition unit. When the ultrasound/photo-acoustic imaging apparatus generates a 3D ultrasound image, a reference cross-section may be set in 3D volume data, and a 2D ultrasound image corresponding to the reference cross-section is derived from the volume data. The 2D ultrasound image may be a B-mode image.

The profile detector 422 detects the profile of a subject from the 2D ultrasound image. The profile may be detected using an edge mask, such as Sobel, Prewitt, Robert, and Canny masks. Alternatively, the profile may be detected from a difference of Eigen values using an edge structure tensor.

The state determiner 423 compares the profile of the subject detected by the profile detector 422 with profile sample information on the subject. The profile sample information on the subject may be stored in a memory device of the control unit 420. In an embodiment, if the user inputs information on a part of the subject to be diagnosed, the state determiner 423 extracts profile sample information on the subject from information on plural profile samples stored in the memory device, thereby comparing the extracted information with the detected profile of the subject.

If a difference between the extracted profile sample information and the detected profile of the subject exceeds a preset threshold value (for example, 70%), it is determined that the ultrasound probe does not come into contact with the subject. Otherwise, it may be determined that contact between the ultrasound probe and the subject occurs.

The determined result of the state determiner 423 may serve as an interlock signal. The signal related to the determined result of the state determiner 423 is input to the light source controller 424, and the light source controller 424 generates a laser by the light source unit 430 in response to the input signal. For example, if the light source unit 430 is set in an interlocked state and the determined result of the state determiner 423 represents that contact between the ultrasound probe and the subject occurs, the signal input to the light source controller 424 is an interlock release signal to release the light source unit 430 from an interlocked state, thereby allowing the light source unit 430 to emit a laser. Conversely, if the light source unit 430 is in an interlock-released state and the determined result of the state determiner 423 represents that contact between the ultrasound probe and the subject does not occur, the signal input to the light source controller 424 is an interlock setting signal to set the light source unit 430 to an interlocked state, thereby stopping laser emission from the light source unit 430.

The laser interlock systems 100, 200, 300 and 400 according to the above-described embodiments are adapted to generate a laser according to whether or not the user wears safety glasses or whether or not contact between the probe and the subject occurs. A laser interlock system according to a further embodiment of the present invention may generate a laser in consideration of whether or not the user wears safety glasses as well as whether or not contact between the probe and the subject occurs. Determination of whether or not the user wears safety glasses and whether or not contact between the probe and the subject occurs is as described above.

A medical appliance according to an aspect of the present invention may include at least one of the above-described laser interlock systems. A medical appliance including the laser interlock system of FIGS. 2 to 8 may include any one of various laser appliances, photo-acoustic imaging apparatuses, or ultrasound/photo-acoustic imaging apparatuses. A medical appliance including the laser interlock system of FIGS. 9 to 15 or a medical appliance including a laser interlock system that considers whether or not the user wears safety glasses as well as whether or not contact between the probe and the subject occurs may include an ultrasound/photo-acoustic imaging apparatus and may include the probe illustrated in FIGS. 10 and 12.

As is apparent from the above description, with a laser interlock system and a control method for the same according to an aspect of the present invention, laser generation is performed only when an inspector or subject correctly wears safety glasses or only during actual use of a photo-acoustic imaging apparatus, which may protect the eyes of the inspector or subject and prevent unnecessary power consumption.

Although the embodiments of the present invention have been shown and described, it would be appreciated by those skilled in the art that changes may be made in these embodiments without departing from the principles and spirit of the invention, the scope of which is defined in the claims and their equivalents. No claim element herein is to be construed under the provisions of 35 U.S.C. 112, sixth paragraph, unless the element is expressly recited using the phrase "means for".

What is claimed is:

1. A laser interlock system comprising:

a sensing unit sensing whether or not contact between a user and *a pair of* safety glasses occurs, *the pair of safety glasses being one of a plurality of pairs of safety glasses which are registered in the laser interlock system*;

a light source unit generating laser radiation;

*an input unit;* and a control unit that determines, based on an output value from the sensing unit, whether the user is wearing the *pair of* safety glasses, and generates an interlock signal to turn on or off the light source unit for selective laser generation in response to a determined result indicating whether the user is wearing the *pair of* safety glasses,

*wherein the control unit determines that the user wears the pair of safety glasses if each of the output values of a left measurement unit of the sensing unit and a right measurement unit of the sensing unit exceeds a preset first threshold value and the output values are maintained for a preset threshold time or more, and*

*wherein the user inputs a selection of one or more pairs of safety glasses among the plurality of pairs of safety glasses registered in the laser interlock system via the input unit.*

2. The system according to claim 1, wherein the sensing unit is mounted to a nose pad of the *pair of* safety glasses.

3. The system according to claim 2, wherein the sensing unit includes a capacitive sensor.

4. The system according to claim 3, wherein the sensing unit includes:

a first substrate;

a ground electrode formed on the first substrate;

a second substrate bonded onto the ground electrode; and a measurement electrode formed on the second substrate.

5. The system according to claim 3, [wherein the sensing unit includes a left measurement unit and a right measurement unit, and]

wherein each of the left measurement unit and the right measurement unit includes:

a first substrate;

a ground electrode formed on the first substrate;

a second substrate bonded onto the ground electrode; and a measurement electrode formed on the second substrate.

[6. The system according to claim 5, wherein the control unit includes:

at least one state determiner determining whether the user is wearing the safety glasses based on output values of the left measurement unit and the right measurement unit; and an interlock signal generator to generate an interlock release signal for the light source unit if a determined result of the state determiner represents that the user is wearing the safety glasses.]

[7. The system according to claim 6, wherein the state determiner determines that the user is wearing the safety glasses if each of the output values of the left measurement unit and the right measurement unit exceeds a preset first threshold value.]

[8. The system according to claim 7, wherein the state determiner determines that the user is wearing the safety glasses normally if each of the output values of the left measurement unit and the right measurement unit exceeds a preset first threshold value and the output values are maintained for a preset threshold time or more.]

[9. The system according to claim 8, wherein the at least one state determiner includes a plurality of state determiners, each of which is mounted to the corresponding safety glasses of a plurality of safety glasses, and wherein the interlock signal generator receives the determined result related to whether or not each user normally wears the corresponding safety glasses from the plurality of state determiners mounted respectively to the plurality of safety glasses.]

[10. The system according to claim 9, wherein the interlock signal generator generates an interlock release signal for the light source unit if the determined results transmitted from the plurality of state determiners represents that each user is wearing the corresponding safety glasses.]

[11. A laser interlock system to control a laser generated from an ultrasound/photo-acoustic imaging apparatus, the system comprising:

a sensing unit sensing contact between a subject and a probe;

a light source unit generating radiation using the laser; and a control unit to control laser radiation generation by the light source unit in response to an output signal from the sensing unit.]

[12. The system according to claim 11, wherein the sensing unit includes a switch mounted to the probe.]

[13. The system according to claim 12, wherein the switch of the sensing unit is turned on or off according to whether or not contact between the probe and the subject occurs.]

[14. The system according to claim 13, wherein the control unit turns on the light source unit if the output value of the sensing unit indicates contact between the probe and the subject occurs.]

[15. The system according to claim 14, wherein the control unit turns off the light source unit if the output value of the sensing unit indicates contact between the probe and the subject does not occur.]

[16. The system according to claim 11, wherein the sensing unit includes a capacitive sensor mounted to a head of the probe.]

[17. The system according to claim 16, wherein the control unit determines whether contact between the probe and the subject occurs based on the output value of the sensing unit, and controls the light source unit in response to the determined result of whether contact between the probe and the subject occurs.]

[18. The system according to claim 17, wherein the control unit is mounted to the probe.]

[19. The system according to claim 18, wherein the control unit determines that contact between the probe and the subject occurs if the output value of the sensing unit exceeds a preset threshold value.]

[20. The system according to claim 19, wherein the control unit turns on the light source unit if the determined result indicates contact between the probe and the subject occurs.]

[21. The system according to claim 20, wherein the control unit turns off the light source unit if the determined result represents that contact between the probe and the subject does not occur.]

[22. The system according to claim 16, wherein the control unit acquires the output value from the sensing unit when a pulse signal is not generated from the probe.]

[23. The system according to claim 16, wherein the sensing unit includes:

a first substrate;

a ground electrode formed on the first substrate;

a second substrate bonded onto the ground electrode; and a measurement electrode formed on the second substrate.]

[24. A laser interlock system to control a laser generated from an ultrasound/photo-acoustic imaging apparatus, the system comprising:

an ultrasound data acquisition unit to acquire ultrasound data of a subject;

a light source unit to generate radiation using the laser; and a control unit to turn on or off the light source unit in response to the acquired ultrasound data.]

[25. The system according to claim 24, wherein the control unit determines whether contact between the subject and a probe occurs using the acquired ultrasound data, and turns on or off the light source unit according to the determined result.]

[26. The system according to claim 25, wherein the control unit includes:

an image generator to generate a 2-Dimensional (2D) ultrasound image using the acquired ultrasound data;

a profile detector to detect a profile of the subject from the 2D ultrasound image; and a state determiner to compare the detected profile of the subject with predetermined profile information corresponding to the subject, so as to calculate a profile difference.]

[27. The system according to claim 26, wherein the state determiner determines that contact between the subject and the probe occurs if the calculated profile difference is less than a preset threshold value.]

[28. The system according to claim 27, wherein the control unit further includes a light source controller to turn on the light source unit if the state determiner determines that contact between the subject and the probe occurs.]

*29. A photoacoustic imaging apparatus comprising: a source configured to generate laser beams;*

*a first bundle of optical fibers and a second bundle of optical fibers, wherein the first bundle of optical fibers and the second bundle of optical fibers are configured to transmit the laser beams generated by the source:*

*a probe configured to receive photoacoustic waves that are generated from an object in response to the object being radiated by the laser beams transmitted by the first bundle of optical fibers and the second bundle of optical fibers: and*

*a holding piece configured to hold the first bundle of optical fibers on a first side of the probe and to hold the second bundle of optical fibers on a second side of the probe opposite to the first side,*

*a first sensor configured to sense whether or not contact between a user and a pair of safety glasses occurs, the pair of safety glasses being one of a plurality of pairs of safety glasses which are registered in the photoacoustic imaging apparatus;*

*a second sensor configured to sense whether or not contact between the probe and the object occurs;*

*an input device; and*

*a controller configured to:*

*determine, based on an output value of the first sensor, whether or not the contact between the user and the pair of safety glasses occurs,*

*determine, based on an output value of the second sensor, whether or not the contact between the probe and the object occurs, and*

*turn on the source in response to both of the contact between the user and the pair of safety glasses and the contact between the probe and the object occurring, and*

*wherein the controller determines that the contact between the user and the pair of safety glasses occurs, if each of the output values of a left measurement unit of the first sensor and a right measurement unit of the first sensor exceeds a preset first threshold value and the output values are maintained for a preset threshold time or more, and*

*wherein the input device receives a user input for a selection of one or more pairs of safety glasses among the plurality of pairs of safety glasses registered in the photoacoustic imaging apparatus.*

*30. The apparatus according to claim 29, wherein one end of the first bundle of optical fibers and one end of the second bundle of optical fibers are configured to be mounted in the holding piece.*

*31. The apparatus according to claim 29, wherein the second sensor comprises a switch mounted to the probe and the switch is turned on or off according to whether or not the contact between the probe and the object occurs.*

*32. The apparatus according to claim 29, wherein the second sensor comprises:*

*a first substrate:*

*a ground electrode formed on the first substrate: a second substrate bonded onto the ground electrode: and*

*a measurement electrode formed on the second substrate, the measurement electrode*

*disposed closer to outside of the probe than the ground electrode.*

*33. The apparatus according to claim 29, wherein the output value of the second sensor is obtained when a pulse signal is not generated from the probe.*

*34. The apparatus according to claim 32, wherein the measurement electrode is disposed closer to outside of the probe than the around electrode.*

* * * * *